United States Patent [19]

Cleland et al.

[11] Patent Number: 5,753,219
[45] Date of Patent: *May 19, 1998

[54] EXCIPIENT STABILIZATION OF POLYPEPTIDES TREATED WITH ORGANIC SOLVENTS

[75] Inventors: Jeffrey L. Cleland, San Carlos; Andrew J. S. Jones, San Mateo, both of Calif.

[73] Assignee: Genentech, Inc., South San Francisco, Calif.

[*] Notice: The term of this patent shall not extend beyond the expiration date of Pat. No. 5,589,167.

[21] Appl. No.: 442,241

[22] Filed: May 15, 1995

Related U.S. Application Data

[63] Continuation of Ser. No. 256,187, Apr. 8, 1994, Pat. No. 5,589,167, which is a continuation-in-part of Ser. No. 21,421, PCT/US94/01666 filed on Feb. 17, 1994, abandoned.

[51] Int. Cl.⁶ .......................... A61K 38/27; A61K 38/21
[52] U.S. Cl. ................ 424/85.7; 514/21; 530/351; 530/399
[58] Field of Search ............... 424/85.7; 514/21; 530/351, 399

[56] References Cited

U.S. PATENT DOCUMENTS

| | | | |
|---|---|---|---|
| 3,664,963 | 5/1972 | Pasin | 252/316 |
| 4,297,233 | 10/1981 | Qualandi | 252/259.5 |
| 4,297,344 | 10/1981 | Schwinn et al. | 424/101 |
| 4,652,441 | 3/1987 | Okada et al. | 424/19 |
| 4,816,568 | 3/1989 | Hamilton | 530/399 |
| 4,891,319 | 1/1990 | Roser | 435/188 |
| 5,032,405 | 7/1991 | Huang et al. | 424/463 |
| 5,039,540 | 8/1991 | Ecanow | 426/385 |
| 5,096,885 | 3/1992 | Pearlman et al. | 514/12 |
| 5,100,669 | 3/1992 | Hyon et al. | 424/426 |
| 5,149,653 | 9/1992 | Roser | 435/260 |
| 5,312,705 | 5/1994 | Aurell et al. | 435/188 |

FOREIGN PATENT DOCUMENTS

| | | | |
|---|---|---|---|
| B-30771/89 | 7/1989 | Australia | A61K 47/18 |
| 0193917 | 9/1985 | European Pat. Off. | A61K 9/18 |
| 251476 | 1/1988 | European Pat. Off. | |
| 256726 | 2/1988 | European Pat. Off. | |
| 0303746 | 2/1989 | European Pat. Off. | A61K 37/36 |
| 0303746 | 8/1989 | European Pat. Off. | |
| WO 87/05300 | 9/1987 | WIPO | |
| WO 89/03671 | 5/1989 | WIPO | A61K 9/18 |
| WO 89/09614 | 10/1989 | WIPO | |
| WO 92/14449 | 9/1992 | WIPO | |
| WO 92/16193 | 10/1992 | WIPO | |
| WO 95/11008 | 4/1995 | WIPO | |
| WO 95/11009 | 4/1995 | WIPO | |
| WO 95/11010 | 4/1995 | WIPO | |

OTHER PUBLICATIONS

Wang et al., J. Parenteral Sci & Tech., vol. 42, No. 2S, pp. S3–S26, 1988.

"Protein Structure", A practical approach, Ed T.E. Creighton, IRL Press, Cahpter 14, 1989.

Manning et al., Pharm. Res., vol. 6(11), pp. 903–918, 1989.

Pikal, Biopharm. vol. 3(9), pp. 26–30, 1990.

Arakawa et al., "Protein–Solvent Interactions in Pharmaceutical Formulations" *Pharmaceutical Research* 8(3) :285–291 (1991).

Cleland, J. et al., "Stabilization of Recombinant Human Growth Hormone Against Denaturation by Methylene Chloride" (Genentech Technical Report) pp. 1–29 (1992).

Colaco, C. et al., "Extraordinary stability of enzymes dried in trehalose: simplified molecular biology" *Bio/Technology* 10 (9) :1007–1011 (1992).

Levine and Slade, "Another View of Trehalose for Drying and Stabilizing Biological Materials" *BioPharm* 5(4) :36–40 (1992).

Roser, B., "Trehalose Drying: A Novel Replacement for Freeze–Drying" *Bio. Pharm.* 4(8) :47–53 (1991).

*Primary Examiner*—Chhaya D. Sayala
*Attorney, Agent, or Firm*—Timothy E. Torchia; Deirdre L. Conley

[57] ABSTRACT

Methods and compositions for excipient stabilization of dry or aqueous polypeptides treated with organic solvents are disclosed, wherein the polypeptide is admixed with a polyol having a molecular weight less than about 70,000 kD.

7 Claims, No Drawings

EXCIPIENT STABILIZATION OF POLYPEPTIDES TREATED WITH ORGANIC SOLVENTS

This is a continuation of application U.S. Ser. No. 08/256,187, filed Apr. 8, 1994, now U.S. Pat. No. 5,589,167, which is a 371 of U.S. Ser. No. PCT/US94/01666 filed on 17 Feb. 1994, which is a CIP of U.S. Ser. No. 08/021,421, filed Feb. 23, 1993, now abandoned.

FIELD OF THE INVENTION

This invention relates to the use of excipients to stabilize both dry and aqueous formulations of polypeptides treated with organic solvents.

BACKGROUND OF THE INVENTION

Pharmaceutical preparations of polypeptides are sensitive to denaturation and degradation upon formulation and storage. Polyols have been used to stabilize proteins and other macromolecules in aqueous formulations and in air drying or lyophilization from aqueous solutions.

U.S. Pat. No. 4,297,344 discloses stabilization of coagulation factors II and VIII, antithrombin III, and plasminogen against heat by adding selected amino acids such as glycine, alanine, hydroxyproline, glutamine, and aminobutyric acid, and a carbohydrate such as a monosaccharide, an oligosaccharide, or a sugar alcohol.

European Patent Application Publication No. 0 303 746 discloses stabilization of growth promoting hormones with polyols consisting of non-reducing sugars, sugar alcohols, sugar acids, pentaerythritol, lactose, water-soluble dextrans, and Ficoll, amino acids, polymers of amino acids having a charged side group at physiological pH, and choline salts.

European Patent Application Publication No. 0 193 917 discloses a biologically active composition for slow release characterized by a water solution of a complex between a protein and a carbohydrate.

Australian Patent Application No. AU-A-30771/89 discloses stabilization of growth hormone using glycine and mannitol.

U.S. Pat. No. 5,096,885 discloses a formulation of hGH for lyophilization containing glycine, mannitol, a non-ionic surfactant, and a buffer.

The use of polyethylene glycols to stabilize proteins is reviewed in *Pharm Res.* 8:285–291, 1991.

Examples of the use of trehalose and other polyols for the stabilization of proteins during drying in aqueous systems include the following.

U.S. Pat. No. 4,891,319 discloses the preservation of sensitive proteins and other macromolecules in aqueous systems by drying at ambient temperatures and at atmospheric pressure in the presence of trehalose.

U.S. Pat. No. 5,149,653 discloses a method of preserving live viruses in an aqueous system by drying in a frozen state or at ambient temperature, in the presence of trehalose.

Polyols have also been used to stabilize dry drug formulations as, for example, in WO 8903671, filed May 5, 1989, which discloses the addition of a stabilizer such a gelatin, albumin, dextran, or trehalose to a mixture of a finely powdered drug suspended in a oily medium.

Treatment of a polypeptide with an organic solvent such as methylene chloride poses the problem of denaturation of the polypeptide of interest. Thus, it is an object of this invention to provide a method for stabilizing polypeptides in aqueous formulations treated with organic solvents.

It is another object of the invention to stabilize dry polypeptides treated with organic solvents.

It is another object of the invention to provide a method for stabilization of encapsulated polypeptides.

It is another object of the invention to provide a polypeptide stabilized by an excipient for use in a controlled release formulation, wherein the polypeptide is treated with an organic solvent.

SUMMARY OF THE INVENTION

One aspect of the invention is a method of stabilizing a polypeptide against denaturation when treated with an organic solvent, wherein the method comprises admixing the polypeptide with a polyol, wherein the molecular weight of the polyol is less than about 70,000 kD.

Another aspect of the invention is a method of formulating a polypeptide comprising a) admixing the polypeptide in an aqueous solution with a polyol having a molecular weight less than about 70,000 kD; and b) treating the polypeptide in the aqueous solution with an organic solvent.

Another aspect of the invention is a method of formulating a dry polypeptide for controlled release comprising a) admixing the polypeptide with an excipient, wherein said excipient is a polyol having a molecular weight less than about 70,000 kD; and b) treating the product of step a) with an organic solvent.

Another aspect of the invention is a composition for controlled release of a polypeptide comprising a polypeptide admixed with an excipient, the excipient being a polyol having a molecular weight less than about 70,000 kD, wherein the polypeptide admixed with the excipient is treated with an organic solvent and is encapsulated in a polymer matrix.

DETAILED DESCRIPTION OF THE INVENTION

A. DEFINITIONS

The term "polyol" as used herein denotes a hydrocarbon including at least two hydroxyls bonded to carbon atoms. Polyols may include other functional groups. Examples of polyols useful for practicing the instant invention include sugar alcohols such as mannitol and trehalose, and polyethers.

The term "polyether" as used herein denotes a hydrocarbon containing at least three ether bonds. Polyethers may include other functional groups. Polyethers useful for practicing the invention include polyethylene glycol (PEG).

The term "dry polypeptide" as used herein denotes a polypeptide which has been subjected to a drying procedure such as lyophilization such that at least 50% of moisture has been removed.

The term "encapsulation" as used herein denotes a method for formulating a therapeutic agent such as a polypeptide into a composition useful for controlled release of the therapeutic agent. Examples of encapsulating materials useful in the instant invention include polymers or copolymers of lactic and glycolic acids, or mixtures of such polymers and/or copolymers, commonly referred to as "polylactides."

The term "admixing" as used herein denotes the addition of an excipient to a polypeptide of interest, such as by mixing of dry reagents or mixing of a dry reagent with a reagent in solution or suspension, or mixing of aqueous formulations of reagents.

The term "excipient" as used herein denotes a non-therapeutic agent added to a pharmaceutical composition to provide a desired consistency or stabilizing effect.

The term "organic solvent" as used herein is intended to mean a carbon compound containing solvent. Exemplary organic solvents include methylene chloride, ethyl acetate, dimethyl sulfoxide, tetrahydrofuran, dimethylformamide, and ethanol.

"Treating" a polypeptide with an organic solvent as used herein refers to mixing a dry polypeptide with an organic solvent, or making an emulsion of a polypeptide in an aqueous formulation with an organic solvent, creating an interface between a polypeptide in an aqueous formulation with an organic solvent, or extracting a polypeptide from an aqueous formulation with an organic solvent.

"Polypeptide" as used herein refers generally to peptides and proteins having more than about 10 amino acids.

B. GENERAL METHODS

In general, both aqueous formulations and dry polypeptides may be admixed with an excipient to provide a stabilizing effect before treatment with an organic solvent. An aqueous formulation of a polypeptide may be a polypeptide in suspension or in solution. Typically an aqueous formulation of the excipient will be added to an aqueous formulation of the polypeptide, although a dry excipient may be added, and vice-versa. An aqueous formulation of a polypeptide and an excipient may be also dried by lyophilization or other means. Such dried formulations may be reconstituted into aqueous formulations before treatment with an organic solvent.

The excipient used to stabilize the polypeptide of interest will typically be a polyol of a molecular weight less than about 70,000 kD. Examples of polyols that maybe used include trehalose, mannitol, and polyethylene glycol. Typically, the mass ratio of trehalose to polypeptide will be 100:1 to 1:100, preferably 1:1 to 1:10, more preferably 1:3 to 1:4. Typical mass ratios of mannitol to polypeptide will be 100:1 to 1:100, preferably 1:1 to 1:10, more preferably 1:1 to 1:2. Typically, the mass ratio of PEG to polypeptide will be 100:1 to 1:100, preferably 1:1 to 1:10. Optimal ratios are chosen on the basis of an excipient concentration which allows maximum solubility of polypeptide with minimum denaturation of the polypeptide.

The formulations of the instant invention may contain a preservative, a buffer or buffers, multiple excipients, such as polyethylene glycol (PEG) in addition to trehalose or mannitol, or a nonionic surfactant such as Tween® surfactant. Non-ionic surfactants include a polysorbate, such as polysorbate 20 or 80, etc., and the poloxamers, such as poloxamer 184 or 188, Pluronic® polyols, and other ethylene/polypropylene block polymers, etc. Amounts effective to provide a stable, aqueous formulation will be used, usually in the range of from about 0.1% (w/v) to about 30% (w/v).

Buffers include phosphate, Tris, citrate, succinate, acetate, or histidine buffers. Most advantageously, the buffer is in the range of about 2 mM to about 100 mM. Preferred buffers include sodium succinate and potassium phosphate buffers.

Preservatives include phenol, benzyl alcohol, metacresol, methyl paraben, propyl paraben, benzalconium chloride, and benzethonium chloride. The preferred preservatives are 0.2–0.4% (w/v) phenol and 0.7–1% (w/v) benzyl alcohol, although the type of preservative and the concentration range are not critical.

In general, the formulations of the subject invention may contain other components in amounts not detracting from the preparation of stable forms and in amounts suitable for effective, safe pharmaceutical administration. For example, other pharmaceutically acceptable excipients well known to those skilled in the art may form a part of the subject compositions. These include, for example, various bulking agents, additional buffering agents, chelating agents, antioxidants, cosolvents and the like; specific examples of these could include trihydroxymethylamine salts ("Tris buffer"), and disodium edetate.

Polypeptides of interest include glycosylated and unglycosylated polypeptides, such as growth hormone, the interferons, and viral proteins such as HIV protease and gp120.

The stabilized polypeptide of the instant invention may be formulated for sustained release, especially as exposure to organic solvents is a common step in many of such preparations. Suitable examples of sustained-release preparations include semipermeable matrices of solid hydrophobic polymers containing the polypeptide, which matrices are in the form of shaped articles, e.g. films, or microcapsules. Examples of sustained-release matrices include polyesters, hydrogels [e.g., poly(2-hydroxyethylmethacrylate) as described by Langer, et al., *J. Biomed. Mater. Res.*, 15:167–277 (1981) and Langer, *Chem. Tech.*, 12:98–105 (1982) or poly(vinylalcohol)], polylactides (U.S. Pat. No. 3,773,919, EP 58,481), copolymers of L-glutamic acid and gamma ethyl-L-glutamate (Sidman, et al., *Biopolymers*, 22:547–556 [1983]), non-degradable ethylene-vinyl acetate (Langer, et al., supra), degradable lactic acid-glycolic acid copolymers such as the Lupron Depot™ (injectable microspheres composed of lactic acid-glycolic acid copolymer and leuprolide acetate), and poly-D-(–)-3-hydroxybutyric acid (EP 133,988). While polymers such as ethylene-vinyl acetate and lactic acid-glycolic acid enable release of molecules for over 100 days, certain hydrogels release polypeptides for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for polypeptide stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release ligand analogs or antibody compositions also include liposomally entrapped polypeptides. Liposomes containing polypeptides are prepared by methods known per se: DE 3,218,121; Epstein, et al., *Proc. Natl. Acad. Sci. USA*, 82:3688–3692 (1985); Hwang, et al., *Proc. Natl. Acad. Sci. USA*, 77:4030–4034 (1980); EP 52,322; EP 36,676; EP 88,046; EP 143,949; EP 142,641; Japanese patent application 83-118008; U.S. Pat. No. 4,485,045 and U.S. Pat. No. 4,544,545; and EP 102,324. Ordinarily the liposomes are of the small (about 200–800 Angstroms) unilamelar type in which the lipid content is greater than about 30 mol. % cholesterol, the selected proportion being adjusted for the optimal ligand analogs therapy. Liposomes with enhanced circulation time are disclosed in U.S. Pat. No. 5,013,556.

EXPERIMENTAL EXAMPLES

EXAMPLE I

Stabilization of Aqueous Formulations

Recombinant human growth hormone (hGH) and recombinant human gamma-interferon (hIFN-γ) were formulated with various excipients for analysis of the excipient effects on stabilization in the organic solvent, methylene chloride. Optimal formulations were generally those that yielded the maximum soluble polypeptide concentration and the greatest recovery of native polypeptide after treatment with methylene chloride. The maximum solubility of hGH in each solution was determined through the continuous addition of hGH lyophilized in ammonium bicarbonate buffer to the solution and the solubility limit was defined as the concentration at which addition of polypeptide resulted in precipitation. The maximum solubility of hIFN-γ was measured by adding a concentrated stock solution (264 mg/ml hIFN-γ, 10 mM Na succinate, pH 5) to concentrated excipient solutions. The apparent solubility limit of hIFN-γ was not observed for any of the formulations at these conditions, but long term storage of the stock solution did result in precipitation as the result of a pH increase (final solution, pH 6). Both polypeptide formulations were tested for stability in methylene chloride by addition of 100 μl of the polypeptide solution to 1 ml of methylene chloride. The mixture was then sonicated for 30 sec. After sonication, the polypeptide was extracted from the organic phase by dilution into 50 ml of excipient-free buffer (50 mM phosphate buffer, pH 8 for hGH; 10 nM succinate buffer, pH 5 for hIFN-γ). The amount of soluble polypeptide recovered was determined by ultraviolet absorbance measurements and the amount of monomeric polypeptide was assessed by size exclusion chromatography.

Both polypeptides were tested for stability with trehalose, mannitol, carboxymethylcellulose (CMC), Tween® 20 surfactant, dextran, gelatin, and polyethylene glycol. Previous studies with hGH indicated that formulations containing an equal mass ratio of polypeptide and mannitol stabilized the polypeptide from denaturation and provided a maximum soluble polypeptide concentration of 200 mg/ml (100 mM phosphate, 200 mg/ml mannitol, pH 8). Trehalose formulations containing mass ratios Of excipient to polypeptide of 1:4 and 1:3 yielded the highest concentration of soluble polypeptide, 400 mg/ml and 300 mg/ml, respectively. In addition, when the lyophilized polypeptide in these formulations was treated with methylene chloride, complete recovery of soluble monomeric hGH was achieved. hGH formulations containing mannitol or mannitol with PEG resulted in similar recovery of monomeric hGH, but the mass ratio (excipient/polypeptide) required to prevent denaturation was greater than that of the trehalose formulations (mannitol: 1:1; mannitol/PEG 1:1 or 1:2; trehalose: 1:3 or 1:4) (Table I). Therefore, trehalose provided high hGH solubility and protection from denaturation in methylene chloride at a lower mass concentration. In the absence of excipients, the solubility of hGH was much lower (about 106 mg/ml) and the polypeptide was more susceptible to denaturation.

TABLE I

Methylene chloride testing of aqueous hGH formulations.

| Formulation[a] | Soluble Monomer Recovered[b] (mg/ml) | Maximum Solubility[c] (mg/ml) |
|---|---|---|
| 100 mg/ml PEG (3350 MW) | 12.2 | 96.4 |
| 50 mg/ml PEG | 34.7 | 89.6 |
| 10 mg/ml PEG | 37.2 | 128.3 |
| 100 mg/ml Mannitol | 66.0 | 98.0 |

TABLE I-continued

Methylene chloride testing of aqueous hGH formulations.

| Formulation[a] | Soluble Monomer Recovered[b] (mg/ml) | Maximum Solubility[c] (mg/ml) |
|---|---|---|
| 50 mg/ml Mannitol | 46.2 | 106 |
| 10 mg/ml Mannitol | 56.0 | 106 |
| 100 mg/ml Dextran 70 | 34.6 | 112.6 |
| 50 mg/ml Dextran 70 | 64.6 | 146.1 |
| 10 mg/ml Dextran 70 | 38.4 | 167.1 |
| 2% CMC | 44.7 | 91.9 |
| 100 mg/ml Trehalose | 113.9 | 267.3 |
| 50 mg/ml Trehalose | 82.8 | 275 |
| 10 mg/ml Trehalose | 92.0 | 267.3 |
| 4 mg/ml PEG (3350 MW), 96 mg/ml Mannitol | 102.6 | 243.7 |
| 10 mg/ml PEG (3350 MW), 90 mg/ml Mannitol | 104.0 | 184 |
| 20 mg/ml PEG (3350 MW) 80 mg/ml Mannitol | 139.9 | 240 |
| 2% Gelatin | 21.9 | 70.5 |
| 100 mg/ml PEG (1000 MW) | 69.2 | 131.5 |
| 50 mg/ml PEG | 84.3 | 246.5 |
| 10 mg/ml PEG | 126.5 | 226.3 |
| 4 mg/ml PEG (1000 MW) 96 mg/ml Trehalose | 122.3 | 230.3 |
| 10 mg/ml PEG (1000 MW) 90 mg/ml Trehalose | 58.4 | 218.7 |
| 20 mg/ml PEG (1000 MW) 80 mg/ml Trehalose | 75.3 | 207.5 |
| No excipient | 65.0 | 106.3 |

[a]All solutions contained 10 mM NaPO4, pH 8.
[b]Polypeptide extracted out of methylene chloride (fraction of total) as determined by absorbance at 278 nm multiplied by the fraction of monomer recovered from SEC-HPLC. Polypeptide treated at maximum solubility.
[c]Maximum solubility was defined as the maximum amount of unformulated hGH that would dissolve in each buffer.

For studies with hIFN-γ, both mannitol and trehalose were the best excipients tested. When mannitol was used at a mass ratio (excipient/polypeptide) of 1:3, the amount of soluble dimer in solution (as determined by size exclusion chromatography) after methylene chloride treatment was equivalent to the amount in the starting material. However, the mannitol formulations yielded less than 60% recovery of total soluble polypeptide. In contrast, the trehalose formulation with a mass ratio of 1:2.5 gave an 80% recovery of total soluble polypeptide and the same fraction of soluble dimer (as determined by size exclusion chromatography, denoted native SEC-HPLC) as the starting material (Table II). Excipient-free polypeptide formulations treated with methylene chloride retained 10% of the initial soluble dimer (as determined by native SEC-HPLC) after methylene chloride treatment and the total soluble polypeptide recovery was less than 60%. When assayed by size exclusion chromatography in 0.2M NaPO₄/0.1% SDS at pH 6.8 (denoted SDS SEC-HPLC), all formulations were greater than 99% monomer before and after methylene chloride treatment.

For both polypeptides, a dramatically lower recovery of monomeric polypeptide was observed after methylene chloride treatment for all formulations containing Tween® 20 surfactant. Although other surfactants have not been studied, it is likely that hydrophobic molecules such as Tween® 20 surfactant stabilize the denatured polypeptides while sugars such as mannitol and trehalose stabilize the native polypeptide.

TABLE II

Methylene chloride testing of aqueous hIFN-γ formulations

| Formulation[a] | % Soluble Polypeptide Recovered[b] | % Intact Dimer[c] | Soluble Dimer[d] |
|---|---|---|---|
| 0.01% Tween® 20* | 36.1 | 49.0 | 11.1 |
| 0.01% Tween® 20* 62 mg/ml Mannitol | 59.0 | 69.0 | 25.6 |
| 5 mg/ml Mannitol | 58.3 | 72.7 | 56.8 |
| 50 mg/ml Mannitol | 62.9 | 83.4 | 70.3 |
| 5 mg/ml Trehalose | 117 | 34.2 | 53.6 |
| 50 mg/ml Trehalose | 75.6 | 61.3 | 62.1 |
| 1% CMC | 78.2 | 62.5 | 65.5 |
| No excipient | 51.6 | 6.0 | 7.9 |

[a]All solutions with excipient contained 134 mg/ml hIFN-γ,10 mM sodium succinate, pH 5; "no excipient" formulation contained 256.3 mg/ml protein, 10 mM sodium succinate, pH 5.0.
[b]Polypeptide extracted out of methylene chloride (fraction of total) as determined by absorbance at 280 nm.
[c]Amount of intact dimer measured by SEC-HPLC native method. All formulations yielded >99% monomer when assayed by the SEC-HPLC SDS method.
[d]Soluble dimer concentration (mg/ml) based on the amount of soluble polypeptide recovered and the fraction of dimer (native SEC-HPLC method).
*Polypeptide concentration in these formulations was 62.8 mg/ml.

EXAMPLE II

Stabilization of Dry and Aqueous Formulations for Encapsulation

In the development of a long acting formulation for recombinant human growth hormone the use of a biodegradable polymeric matrix for sustained release of hGH was investigated. The polymer used for this application was a copolymer of lactic and glycolic acids which is often referred to as poly(lactic/glycolic acid) or PLGA. To incorporate hGH into this polymer, the PLGA must be dissolved in a water immiscible solvent. The most commonly used solvent for dissolution of PLGA has been methylene chloride which provides both water immiscibility and PLGA solubility.

In general, for production of hGH-PLGA microspheres, the polypeptide was added to a solution of methylene chloride containing PLGA. In initial studies, the polypeptide was added in the form of a milled lyophilized powder. After polypeptide addition, the methylene chloride solution was then briefly homogenized and the solution was added to an emulsification bath. This process resulted in the extraction of methylene chloride with the concomitant formation of PLGA microspheres containing hGH. The polypeptide released from these microspheres was then studied to determine the integrity of hGH after incorporation into the microspheres. Assessment of released hGH was performed by analytical size exclusion chromatography (SEC-HPLC) as well as other techniques. Size exclusion chromatography indicated that hGH was released from the PLGA microspheres in the form of the native monomer, aggregates, and an unknown structure which eluted between the monomer and dimer. The unknown polypeptide structure has been extensively studied and has been shown to be a conformational variant of hGH. In addition, the same aggregates and conformational variant can be obtained by treatment of hGH with methylene chloride. Thus, the use of methylene chloride in the process may cause denaturation and aggregation of hGH.

The release of monomeric native hGH from the PLGA microspheres is required for a successful long acting formulation. Previous studies investigated several organic solvents as alternatives to methylene chloride. This research indicated that hGH was susceptible to damage by several organic solvents. Since methylene chloride provided the desired solvent properties (i.e. water immiscibility, PLGA dissolution, etc.) for PLGA microsphere production and other solvents did not significantly improve hGH stability, methylene chloride was chosen for the production of the PLGA microspheres. The polypeptide used for the solvent study and in the PLGA production process was formulated and lyophilized in ammonium bicarbonate buffer at pH 7. Therefore, this study was performed to develop formulations which would stabilize hGH during the production of the PLGA microspheres.

A. Methods

1. Preparation of hGH Formulations

For development of a methylene chloride stable formulation, hGH lyophilized in ammonium bicarbonate was reconstituted in the desired buffer and allowed to dissolve. Undissolved polypeptide was removed by centrifugation at 13,000 rpm for 1 min.

For each lyophilization, indicted below, the hGH concentration was 10 mg/ml. The residual moisture of these formulations was not determined, but the same lyophilization cycle was used in each case.

Milling of lyophilized protein was performed with a pressure driven impaction mill and resulted in a fine particulate of hGH.

2. Methylene Chloride Testing of hGH Formulations

The effect of methylene chloride on hGH stability was determined by adding hGH to a solution of methylene chloride. For solid hGH conditions, the ratio of polypeptide mass (mg) to volume of organic solvent (ml) was 40 mg/ml. For the aqueous hGH conditions, 100 μl of hGH in a buffered solution was added to 1.0 ml of methylene chloride to assess the effects of each buffer system on stabilization of hGH in methylene chloride. After polypeptide addition, the samples were sonicated for 30 seconds in a 47 kHz bath sonicator (Cole Parmer, Model 08849-00) to simulate the homogenization step in the microsphere production process. If the formulation stabilized hGH against denaturation in this test, it was further assessed by homogenization in methylene chloride. After sonication or homogenization, the polypeptide was extracted from the methylene chloride by dilution into a 50 fold excess of 5 mM NaHPO$_4$, pH 8. The amount and quality of the polypeptide extracted in this step was determined by polypeptide concentration measurements (absorbance at 278 nm) and size exclusion HPLC (SEC-HPLC). The preferred stable formulation was one that yielded the maximum recovery of monomeric polypeptide without the formation of conformational variants or aggregates larger than dimers.

B. Results

1. Excipient Studies of hGH Stabilization

Initial studies of hGH lyophilized in ammonium bicarbonate investigated the solubility of the polypeptide in different buffers at various pH conditions. From these studies, it was determined that hGH had the maximum stability and solubility in phosphate buffer (5–10 mM) at pH 8, and thus additional studies were performed with hGH in this buffer.

Initial attempts to prevent aggregation of hGH utilized Tween® 80 surfactant in the formulation buffer. As shown in Table III, methylene chloride testing of these aqueous formulations indicated that low Tween® surfactant concentrations (0.1% Tween® 80 surfactant) with 10 mg/ml mannitol provided good recovery of soluble monomeric polypeptide.

However, the best results in this experiment were obtained for hGH which was formulated in 10 mg/ml mannitol without Tween® 80 surfactant (5 mM NaHPO$_4$, pH 8). Higher concentrations of Tween® surfactant in the formulation buffer resulted in increased aggregation and decreased recovery of soluble polypeptide. For each case shown in Table III, the formulations provided greater stabilization of hGH than the milled polypeptide which was lyophilized in ammonium bicarbonate.

TABLE III

Methylene chloride testing of aqueous hGH formulations

| Formulation[a] | % Polypeptide[b] Recovered | % Area[c] Recovery | Soluble Polypeptide (Mass Fraction of Total) | | | |
|---|---|---|---|---|---|---|
| | | | % Trimer | % Dimer | % Intermediate | % Monomer |
| 1% Tween® 80 | 85.7 | 90.0 | 0.5 | 3.4 | 1.1 | 94.9 |
| 0.1% Tween® 80 | 70.9 | 98.3 | 2.0 | 3.6 | 1.8 | 92.6 |
| 1% Tween® 80 10 mg/ml Mannitol | 65.0 | 97.8 | 3.3 | 3.4 | 3.4 | 90.0 |
| 0.1% Tween® 80 10 mg/ml Mannitol | 70.9 | 98.3 | 0.0 | 2.2 | 0.0 | 97.8 |
| 10 mg/ml PEG (3350 MW) | 97.6 | 101.1 | 0.0 | 2.6 | 0.0 | 97.4 |
| 10 mg/ml PEG 10 mg/ml Mannitol | 76.4 | 97.7 | 1.7 | 2.8 | 1.6 | 93.9 |
| 5 mM NaPO4, pH 8 | 55.3 | 99.4 | 0.0 | 3.2 | 0.0 | 96.8 |
| 5 mM NaPO4, pH 8 10 mg/ml Mannitol | 91.7 | 99.8 | 0.0 | 1.8 | 0.0 | 98.2 |

[a]All solutions contain 5 mM NaPO$_4$, pH 8
[b]Polypeptide extracted out of methylene chloride (fraction of total) as determined by absorbance at 278 nm.
[c]SEC-HPLC results for polypeptide extracted into buffer after methylene chloride treatment Methylene chloride testing of solid hGH formulations are shown in Table IV. These results indicated that the formulation which best stabilized the protein was 5 mM KPO$_4$, 2.5 mg/ml trehalose.

TABLE IV

Methylene chloride testing of solid rhGH formulations

| Formulation[a] | % Protein[b] Recovered | % Area[c] Recovery | Soluble Protein (Mass Fraction of Total) | | | |
|---|---|---|---|---|---|---|
| | | | % Trimer | % Dimer | % Intermediate | % Monomer |
| Milled Solids | | | | | | |
| NH$_4$CO$_3$ | 44.5 | 85.4 | 7.5 | 5.9 | 7.3 | 79.2 |
| 5 mM NaPO$_4$, pH 8 | 85.7 | 100. | 0.0 | 2.1 | 0.0 | 97.8 |
| 5 mM NaPO$_4$, pH 8 10 mg/ml Mannitol | 87.6 | 100. | 0.0 | 3.0 | 0.0 | 97.0 |

TABLE IV-continued

Methylene chloride testing of solid rhGH formulations

| Formulation[a] | % Protein[b] Recovered | % Area[c] Recovery | Soluble Protein (Mass Fraction of Total) | | | |
|---|---|---|---|---|---|---|
| | | | % Trimer | % Dimer | % Intermediate | % Monomer |
| Homogenized Solids[d] | | | | | | |
| 5 mM KPO$_4$, pH 8, 2.5 mg/ml Trehalose | 97.3 | 100. | 0.0 | 2.2 | 0.0 | 97.8 |
| 5 mM NaPO$_4$, pH 8 | 96.8 | 100. | 0.0 | 2.0 | 0.0 | 98.0 |
| 10 mg/ml Mannitol 0.3 M Na Succinate, 10 mg/ml Mannitol, pH 7 | 94.3 | 100. | 0.0 | 4.2 | 0.0 | 95.8 |

[a]All samples lyophilized at 10 mg/ml rhGH with buffer and excipients as shown.
[b]Protein extracted out of methylene chloride (fraction of total) as determined by absorbance at 278 nm.
[c]SEC-HPLC results for protein extracted into buffer after methylene chloride treatment.
[d]Solid lyophilized formulations were homogenized in methylene chloride at 25,000 rpm for 1 min.

Further studies were performed to determine whether a surfactant could stabilize the methylene chloride-polypeptide interface. Thus, Tween® surfactant was added to the methylene chloride phase and mixed with solid hGH (KPO$_4$, pH 8). The addition of Tween® surfactant to the methylene chloride phase did not improve the stability of the solid-hGH (KPO$_4$, pH 8) as shown in Table V. In addition, the use of the surfactant, Span® 80 surfactant, in the methylene chloride phase did not improve the stability of the solid hGH (KPO$_4$, pH 8). Further attempts with Tween® surfactant in the methylene chloride phase were unsuccessful for the more stable solid hGH formulation (Mannitol, KPO$_4$, pH 8). These results along with the aqueous studies indicated that Tween® surfactant is preferably not used with these formulations since it promotes aggregation and decreases the solubility of methylene chloride treated hGH.

TABLE V

Effect of Tween ® surfactant in the methylene chloride phase on solid hGH stability

| Tween® in MeCl$_2$ | % Polypeptide[a] Recovered | % Area[b] Recovery | Soluble Polypeptide (Mass Fraction of Total) | | | |
|---|---|---|---|---|---|---|
| | | | % Trimer | % Dimer | % Intermediate | % Monomer |
| 0.01% Tween® 80 | 40.8 | 98.7 | 5.2 | 13.0 | 0.0 | 81.8 |
| 0.1% Tween® 80 | 40.8 | 102.9 | 8.0 | 14.0 | 0.0 | 77.9 |
| 1% Tween® 80 | 53.8 | 97.3 | 7.0 | 11.6 | 0.0 | 81.4 |

TABLE V-continued

Effect of Tween ® surfactant in the
methylene chloride phase on solid hGH stability

|  | Soluble Polypeptide (Mass Fraction of Total) | | | | | |
|---|---|---|---|---|---|---|
| Tween® in MeCl$_2$ | % Polypeptide[a] Recovered | % Area[b] Recovery | % Trimer | % Dimer | % Intermediate | % Monomer |

[a]Polypeptide extracted out of methylene chloride (fraction of total) as determined by absorbance at 278 nm.
[b]SEC-HPLC results for polypeptide extracted into buffer after methylene chloride treatment To increase the amount of polypeptide loaded into the microspheres, the amount of excipient should be minimized. Therefore, lower concentrations of mannitol (2 and 5 mg/ml) with 10 mg/ml hGH were used in the formulation buffer (10 mM NaHPO$_4$, pH 8) and the aqueous solutions were tested for methylene chloride stability. These mannitol concentrations yielded 20% less soluble monomer than the 10 mg/ml mannitol formulation. Significant reductions in the mannitol concentration would sacrifice the quality of the released polypeptide. Alternative excipients at lower concentrations were also attempted. Carboxymethylcellulose (CMC) at 0.5, 2, and 5 mg/ml was used in the aqueous formulation (10 mg/ml hGH, 10 nM NaHPO$_4$, pH 8). CMC at 0.5 mg/ml provided the same fraction of soluble monomer as the 10 mg/ml mannitol formulation, but the amount of polypeptide recovered in the aqueous phase was 15% lower. Equal mass mixtures of CMC and mannitol (1 mg/ml and 2.5 mg/ml of each) were also attempted to provide stability at lower excipient concentrations. The use of 2.5 mg/ml of each excipient provided comparable results to the 10 mg/ml mannitol formulation. The 0.5 mg/ml CMC and 2.5 mg/ml each of CMC and mannitol formulations were therefore lyophilized to assess their use for microencapsulation.

To assess formulations for use in the aqueous form, each lyophilized material was reconstituted to the maximum solubility which was defined as the polypeptide concentration where additional polypeptide would not dissolve in the solution. The maximum concentration of hGH in this experiment was achieved with the formulation lyophilized in 10 mg/ml mannitol. This formulation was successfully reconstituted with 5 mM NaHPO$_4$ buffer, pH 8 to 200 mg/ml of hGH (200 mg/ml mannitol, 100 mM KPO$_4$) without precipitation of the polypeptide. The formulation without excipients (KPO$_4$, pH 8) provided the second best solubility at 165 mg/ml of hGH. However, attempts to reconstitute the CMC and CMC/mannitol formulations at high polypeptide concentrations were not successful. In both cases, the formulation formed a paste at concentrations greater than 100 mg/ml. Methylene chloride testing of the pastes formed from the CMC and CMC/mannitol formulations revealed that the amount of polypeptide recovered was significantly reduced (less than 75% recovery) compared to the mannitol formulation, but the soluble fraction was greater than 95% monomer. Since a gel-like formulation may have utility for stabilizing the inner aqueous phase in the process, another thickening agent, gelatin was also attempted. To maintain a low excipient concentration while still obtaining a gel for the final formulation (200 mg/ml hGH), the gelatin formulation was tested at 0.5 mg/ml gelatin, 10 mg/ml hGH, 10 mM KPO$_4$, pH 8. Methylene chloride testing of this formulation yielded recovery of soluble monomer which was comparable to the 10 mg/ml mannitol formulation. Therefore, this formulation was also lyophilized for further analysis.

Reconstitution of the lyophilized polypeptide at 200 mg/ml hGH (10 mg/ml gelatin, 100 mM KPO$_4$, pH 8) resulted in the formation of a paste which had properties similar to those of the CMC/mannitol and CMC formulations at the same hGH concentration.

EXAMPLE III

Stability of rhGH Formulations in Ethyl Acetate

Microencapsulation of proteins in biodegradable polymers often requires the use of organic solvents to solubilize the polymer. The polymer, typically PLGA, polylactide (PLA), or polyglycolide (PGA), is first dissolved in an organic solvent that is not completely miscible with water. The common organic solvents used in this process are methylene chloride and ethyl acetate. These two solvents have very different physical and chemical properties. Therefore, it was necessary to assess the stability of rhGH formulations in both solvents.

The testing of rhGH formulations for stability in ethyl acetate was performed by a method similar to the one used for the methylene chloride studies in the examples above. Solutions of rhGH at 10 mg/ml were prepared by adding lyophilized solid rhGH (ammonium bicarbonate formulation) to each formulation. As shown in Table VI, the formulations were prepared with 5 mM KPO$_4$, pH 8 and contained different excipients. PEG (3350 MW), mannitol, trehalose, and Tween® 20, or combinations of excipients. Each rhGH formulation (100 uL) was added to 1 mL of ethyl acetate and sonicated for 30 sec to form an emulsion. This emulsion was then mixed with 10 mL of 5 mM KPO$_4$, pH 8 resulting in an overall dilution of rhGH by 100 fold. The rhGH extracted into the buffer was analyzed by size exclusion HPLC. Several formulations yielded greater than 100% recovery of soluble protein indicating that the amount of protein added to the emulsion was greater than the estimated amount (0.1 mL×10 mg/mL=1 mg) as the result of the accuracy in volume measurements. In addition, the recovery of soluble protein and the amount of monomer recovered were generally greater than the rhGH in the same formulation treated with methylene chloride. Overall, the recovery of soluble protein was greatest for trehalose (1 & 2 mg/mL), trehalose with PEG (10 mg/mL each), mannitol with PEG (10 mg/mL each) and mannitol with Tween® 20 (10 mg/mL each). However, only the trehalose (1 & 2 mg/ml) and the mannitol with Tween® 20 (10 mg/mL each) also had a high monomer content (greater then 97%). The mannitol/Tween® 20 formulation does not allow adequate solubility for a double emulsion microencapsulation process and it requires a 4:1 excipient to protein ratio (by mass). Thus, the optimum formulation in these experiments was the 1 mg/mL trehalose formulation (1:10 excipient to protein ratio and high rhGH solubility).

TABLE VI

Ethyl acetate testing of aqueous rhGH
formulations as described in the text.

| Formulation[a] | Soluble Protein (Mass Fraction of Total) | | | |
|---|---|---|---|---|
|  | % Recovery[b] Soluble | % Large Aggreg. | % Dimer | % Monomer |
| No excipient | 98.9 | 2.3 | 3.2 | 94.5 |
| 10 mg/mL PEG (3350 | 99.8 | 2.7 | 2.3 | 94.9 |

TABLE VI-continued

Ethyl acetate testing of aqueous rhGH formulations as described in the text.

| Formulation[a] | % Recovery[b] Soluble | % Large Aggreg. | % Dimer | % Monomer |
|---|---|---|---|---|
| 5 mg/mL PEG (MW) | 108.5 | 1.7 | 3.0 | 95.2 |
| 2 mg/mL PEG | 107.2 | 1.8 | 3.8 | 94.3 |
| 10 mg/mL Mannitol | 96.6 | 1.7 | 3.6 | 94.7 |
| 2 mg/mL Mannitol | 86.3 | 4.1 | 3.8 | 92.2 |
| 10 mg/mL Trehalose | 100.1 | 1.8 | 4.5 | 93.7 |
| 2 mg/mL Trehalose | 119.8 | 0.4 | 2.0 | 97.7 |
| 1 mg/mL Trehalose | 111.1 | 0.6 | 2.3 | 97.1 |
| 10 mg/mL PEG (3350 MW) 10 mg/mL Trehalose | 115.6 | 3.8 | 2.9 | 93.3 |
| 2 mg/mL PEG (3350 MW) 2 mg/mL Trehalose | 93.0 | 0.8 | 3.1 | 96.1 |
| 1 mg/mL PEG (3350 MW) 1 mg/mL Trehalose | 95.8 | 4.5 | 3.3 | 92.2 |
| 10 mg/mL PEG (3350 MW) 10 mg/mL Mannitol | 116.3 | 1.2 | 2.5 | 96.3 |
| 2 mg/mL PEG (3350 MW) 2 mg/mL Mannitol | 106.5 | 1.7 | 2.7 | 95.6 |
| 0.1% Tween® 20 10 mg/mL Mannitol | 122.8 | 0.8 | 1.6 | 97.6 |

[a]All initial test solutions contained 10 mg/mL rhGH and 5 mM $KPO_4$, pH 8 except three of the formulations which were at rhGH concentrations less than 10 mg/mL (no excipient: 9.39 mg/mL; 10 mg/mL mannitol/10 mg/mL PEG: 7.84 mg/mL; 10 mg/mL mannitol: 9.71 mg/mL).
[b]SEC-HPLC results for protein extracted into buffer after ethyl acetate treatment. The percent recovery of soluble protein was defined as the ratio of the concentrations from the total peak area of the sample and the appropriate controls (same formulation) times 100%. The control rhGH concentration was determined by absorbance at 278 nm and the sample rhGH concentration was calculated as a 100 fold dilution of the stock material based on the dilutions used in the overall method (0.1 mL in 1 mL EtAc added to 10 mL buffer).

EXAMPLE IV

Stability of Spray Dried rhGH Formulations in Organic Solvents

The double emulsion technique (water-in-oil-in-water) for microencapsulation can only provide moderate loading of drug in the final product. The drug loading is limited by the solubility of the drug in water and the volume of aqueous drug that can be added to the polymer in organic solvent. Volumes of greater than 0.5 mL of drug per gram of polymer typically result in a large initial burst of drug from the microspheres. To avoid these difficulties, a solid drug formulation can be used in place of the aqueous drug solution. Thus, a solid-in-oil-in-water process can be used to produce microspheres with high drug loading (greater then 10%) with low to moderate initial bursts.

The solid drug formulation used for microencapsulation must be stable in organic solvents and it must have a small size (1–5 μm) relative to the microspheres (30–100 μm) to permit high loading and low burst of the drug. For protein formulations, one method of obtaining small dried solids is spray drying. A recent report by Mummenthaler et al., Pharm. Res. 11(1):12–20 (1994) describes the process of spray drying rhGH formulations. Since rhGH is easily denatured by surface interactions such as air-liquid interfaces, the spray drying of rhGH must be performed with surfactants in the rhGH formulation. However, as noted above, the presence of some surfactants can have a negative effect on the stability of rhGH in methylene chloride. Spray dried rhGH formulations with different surfactants and trehalose, which were above observed to be the best for stabilization of the aqueous rhGH formulations, were tested for stability in methylene chloride and ethyl acetate.

Spray dried rhGH was prepared from each of the formulations listed in Table VII. These formulations were sprayed at 5 mL/min with an inlet temperature of 90° C., an air nozzle flow rate of 600 L/hr, and a drying air rate of 36,000 L/hr. The spray dried rhGH was then collected from the filter and the cyclone units of the spray drier. The final solid usually was approximately 5 μm in diameter.

The spray dried rhGH powder was then tested for stability by treatment with either ethyl actate or methylene chloride. A spray dried powder mass equivalent to 10 mg of rhGH was added to 2 mL of the organic solvent in a 3 cc glass test tube. The suspension was next homogenized at 10,000 rpm for 30 sec with a microfine homogenization tip. After mixing, 20 μL of the homogeneous suspension was added to 980 μL of 5 mM $KPO_4$, pH 8 to extract out the protein. The extracted protein concentration was determined by absorbance at 278 nm and the sample was also analyzed by size exclusion chromatography. As shown in Table VII, the formulation without surfactant had the greatest extent of aggregation when treated with methylene chloride. This aggregation was likely the result of the surface denaturation of rhGH during the drying process as previously observed for spray drying of rhGH. By adding either Tween® 20 or PEG (3350 MW) to the formulation, the amount of aggregation for the methylene chloride treated samples was reduced, but the overall recovery yield was still low and the monomer content was much less than 90%. In contrast, if the same spray dried rhGH formulations containing surfactant were treated with ethyl acetate, the amount of aggregation was neglible and complete recovery of monomeric rhGH was achieved. Therefore, spray dried rhGH formulations consisting of trehalose and either Tween® 20 or PEG (3350 MW) were stable in ethyl acetate but did not protect the protein from denaturation in methylene chloride.

TABLE VII

Stability of spray dried solid rhGH formulations in methylene chloride and ethyl acetate.

| Formulation | % Recovery[a] (Total) | % Recovery[b] (Soluble) | % Large Aggreg | % Dimers | % Monomer |
|---|---|---|---|---|---|
| Methylene Chloride Tests | | | | | |
| 15 mg/mL rhGH 3.75 mg/mL trehalose | — | — | 12.3 | 8.8 | 75.4 |
| 10 mg/ml rhGH 2.5 mg/mL trehalose 0.2% Tween® 20 | 56.5 | 65.2 | 1.9 | 13.3 | 78.1 |
| 10 mg/mL rhGH 2.5 mg/mL trehalose 0.2% PEG (3350 MW) | 50.7 | 56.7 | 3.9 | 12.3 | 77.7 |
| Ethyl Acetate Tests | | | | | |
| 10 mg/mL rhGH 2.5 mg/mL trehalose 0.2% Tween® 20 | 111.7 | 126.8 | 0.9 | 0.0 | 99.2 |
| 10 mg/mL rhGH 2.5 mg/mL trehalose 0.2% PEG (3350 MW) | 114.3 | 125.5 | 1.1 | 0.0 | 98.9 |
| 5.0 mg/mL rhGH 1.25 mg/mL trehalose 0.2% Tween® 20 | 106.8 | 110.4 | 0.3 | 3.0 | 96.7 |

TABLE VII-continued

Stability of spray dried solid rhGH formulations in methylene chloride and ethyl acetate.

|  | | Soluble Protein | | | |
|---|---|---|---|---|---|
| Formulation | % Recovery[a] (Total) | % Recovery[b] (Soluble) | % Large Aggreg | % Dimers | % Monomer |

[a]The total recovery of protein was defined as the amount of protein extracted into buffer after treatment in the organic solvent divided by the calculated amount of protein added to the extraction buffer (0.02 mL × 5 mg/mL).
[b]SEC-HPLC results for protein extracted into buffer after treatment with organic solvent. The percent recovery of soluble protein was defined as the ratio of the concentrations from the total peak area of the sample and a reference standard times 100%. The control and sample rhGH concentrations were determined by absorbance at 278 nm.

EXAMPLE V

Stability of Spray Freeze-Dried rhGH Formulations in Methylene Chloride and Ethyl Acetate Spray drying at high temperatures can have a detrimental effect on the protein and it produces protein particles which are often hollow spheres (Mummenthaler et al., *Pharm. Res.* 11(1):12–20 (1994). In addition, it is difficult to collect the small particles 1–5 μm) required for microencapsulation and the overall yield of these particles is usually very low (less than 50%). An alternative to high temperature spray drying is spray freeze-drying. Spray freeze-drying of rhGH formulations results in a fine particles (2–3 μm) that readily break apart into very small solids (less than 1 μm). This type of solid formulation is preferred for microencapsulation in a polymer matrix since it can provide a high loading (able to pack more solid into 30–100 μm microspheres) of homogeneously dispersed solid protein (reduced burst due to fine suspension).

Spray freeze-drying of rhGH was performed with the formulations listed in Table VIII. Again, a surfactant was required to stabilize rhGH during the spraying process but other proteins which are not easily denatured by surface interactions would probably not require the use of a surfactant. The spray freeze-dried rhGH was prepared by pumping the formulation at 5 mL/min and operating the air nozzle at 600 L/hr as used for high temperature spray drying (Mummenthaler et al., *Pharm. Res.* 11(1):12–20 1994). The solutions were sprayed into an open metal tray of liquid nitrogen. After spraying, the tray was placed in a prechilled lyophilizer set at –30° C. The liquid nitrogen was allowed to evaporate and the protein was then lyophilized (primary drying: –30° C., 100 mTorr, 52 hrs; secondary drying: 5° C., 100 mTorr, 18 hrs). The final powder was then removed and placed in sealed glass vials prior to use.

The spray freeze-dried rhGH powder was then tested for stability by treatment with ethyl actate and methylene chloride. A spray freeze-dried powder mass equivalent to 10 mg of rhGH was added to 2 mL of the organic solvent in a 3 cc glass test tube. The suspension was next homogenized at 10,000 rpm for 30 sec with a microfine homogenization tip. After mixing, 20 μL of the homogeneous suspension was added to 980 μL of 5 mM KPO$_4$, pH 8 to extract out the protein. The extracted protein concentration was determined by absorbance at 278 nm and the sample was also analyzed by size exclusion chromatography. As shown in Table VIII, the spray freeze-dried formulation containing PEG was more stable in methylene chloride than the formulation containing Tween® 20 as observed above with the aqueous formulations. However, both formulations did not yield high recovery of monomeric rhGH. When these same formulations were treated with ethyl acetate, complete recovery of monomeric protein was achieved with both formulations. The trehalose in the formulations provided stabilization against organic solvent denaturation (ethyl acetate) while the surfactants stabilized the protein against surface denaturation during spray freeze-drying. Thus, spray freeze dried formulations containing both trehalose and a surfactant will yield complete recovery of rhGH from ethyl acetate.

TABLE VIII

Stability of spray freeze-dried solid rhGH formulations in methylene chloride and ethyl acetate.

| | | | Soluble Protein | | |
|---|---|---|---|---|---|
| Formulation | % Recovery[a] (Total) | % Recovery[b] (Soluble) | % Large Aggreg | % Dimers | % Monomer |
| Methylene Chloride Tests | | | | | |
| 5 mg/mL rhGH 1.25 mg/mL trehalose 0.2% Tween ® 20 | 37.2 | 34.0 | 6.2 | 8.3 | 85.5 |
| 5 mg/ml rhGH 1.25 mg/mL trehalose 0.2% PEG (3350 MW) | 68.8 | 66.8 | 2.3 | 15.8 | 78.8 |
| Ethyl Acetate Tests | | | | | |
| 5 mg/mL rhGH 1.25 mg/mL trehalose 0.2% Tween ® 20 | 94.6 | 117.7 | 0.5 | 0.9 | 98.7 |
| 5 mg/ml rhGH 1.25 mg/mL trehalose 0.2% PEG (3350 MW) | 97.7 | 104.7 | 0.6 | 0.0 | 99.4 |

[a]The total recovery of protein was defined as the amount of protein extracted into buffer after treatment in the organic solvent divided by the calculated amount of protein added to the extraction buffer (0.02 mL × 5 mg/mL).
[b]SEC-HPLC results for protein extracted into buffer after treatment with organic solvent. The percent recovery of soluble protein was defined as the ratio of the concentrations from the total peak area of the sample and a reference standard times 100%. Control and sample rhGH concentrations were determined by absorbence at 278 nm.

What is claimed is:

1. A composition for controlled release of a polypeptide, the composition comprising a polypeptide admixed with an excipient, an organic solvent, and a polymer matrix, wherein the excipient is trehalose.

2. The composition of claim 1 wherein the polypeptide admixed with the excipient is in an aqueous formulation.

3. The composition of claim 1 wherein the polypeptide admixed with the excipient is dry.

4. The composition of claim 1 wherein the polypeptide admixed with the excipient is lyophilized.

5. The composition of claim 1, wherein the polymer is a polylactide.

6. The composition of claim 1, further comprising a buffer.

7. The composition of claim 6, further comprising a preservative.

* * * * *